(12) United States Patent
Cordie et al.

(10) Patent No.: US 11,644,561 B2
(45) Date of Patent: May 9, 2023

(54) METHOD OF OPERATING A RADAR SENSOR SYSTEM FOR VITAL SIGN DETECTION WITH ELIMINATION OF SIGNALS EXCITED BY INTERFERING MOVEMENTS

(71) Applicant: IEE INTERNATIONAL ELECTRONICS & ENGINEERING S.A., Echternach (LU)

(72) Inventors: Janine Cordie, Echternacherbrueck (DE); Jochen Landwehr, Trier (DE); Parth Raj Singh, Luxembourg (LU); Dimitri Tatarinov, Trier (DE)

(73) Assignee: IEE INTERNATIONAL ELECTRONICS & ENGINEERING S.A., Echternach (LU)

( * ) Notice: Subject to any disclaimer, the term of this patent is extended or adjusted under 35 U.S.C. 154(b) by 0 days.

(21) Appl. No.: 17/796,174

(22) PCT Filed: Jan. 25, 2021

(86) PCT No.: PCT/EP2021/051560
§ 371 (c)(1),
(2) Date: Jul. 28, 2022

(87) PCT Pub. No.: WO2021/151812
PCT Pub. Date: Aug. 5, 2021

(65) Prior Publication Data
US 2023/0047069 A1    Feb. 16, 2023

(30) Foreign Application Priority Data
Jan. 28, 2020   (LU) .............................. LU 101 622

(51) Int. Cl.
*G01S 13/58*     (2006.01)
*A61B 5/00*      (2006.01)
(Continued)

(52) U.S. Cl.
CPC .............. *G01S 13/584* (2013.01); *A61B 5/05* (2013.01); *A61B 5/6893* (2013.01);
(Continued)

(58) Field of Classification Search
CPC ....... G01S 13/584; A61B 5/05; A61B 5/6893; A61B 5/7207; A61B 5/7246; A61B 5/7282; A61B 5/1102; A61B 5/113
See application file for complete search history.

(56) References Cited

U.S. PATENT DOCUMENTS

| | | | |
|---|---|---|---|
| 6,753,780 B2 | 6/2004 | Li | |
| 7,036,390 B2 * | 5/2006 | Tsuchihashi | G01V 3/12 73/865.9 |

(Continued)

FOREIGN PATENT DOCUMENTS

| | | |
|---|---|---|
| WO | 2015140333 A1 | 9/2015 |
| WO | 2016038148 A1 | 3/2016 |

(Continued)

OTHER PUBLICATIONS

Search Report corresponding to International Application PCT/EP2021/051560; dated Apr. 6, 2021; 3 pages.

(Continued)

*Primary Examiner* — Timothy X Pham
(74) *Attorney, Agent, or Firm* — Reising Ethington P.C.

(57) ABSTRACT

A method of operating a radar sensor system that is configured to determine range and velocity information from radar waves reflected by a scene in an interior of a vehicle for vital sign detection. The method includes steps to decompose reflected and received signals into range and velocity information, to measure the movement over time in specified range gates and to evaluate the similarities between them. Based on the characteristics of similar behaving range bins, (Continued)

it can be decided whether any detected movement is related to an internal or external disturbance or by vital signs.

10 Claims, 4 Drawing Sheets

(51) Int. Cl.
  *A61B 5/05* (2021.01)
  *A61B 5/113* (2006.01)
  *A61B 5/11* (2006.01)
(52) U.S. Cl.
  CPC .......... *A61B 5/7207* (2013.01); *A61B 5/7246* (2013.01); *A61B 5/7282* (2013.01); *A61B 5/1102* (2013.01); *A61B 5/113* (2013.01)

(56) References Cited

U.S. PATENT DOCUMENTS

| | | | | |
|---|---|---|---|---|
| 10,214,118 | B1* | 2/2019 | Jain | B60K 35/00 |
| 11,117,515 | B2* | 9/2021 | Ishibashi | B60Q 9/00 |
| 2003/0201894 | A1* | 10/2003 | Li | B60N 2/002 |
| | | | | 340/457 |
| 2010/0225764 | A1* | 9/2010 | Nizko | G01S 13/04 |
| | | | | 348/152 |
| 2015/0129343 | A1* | 5/2015 | Teng | B60R 21/01534 |
| | | | | 180/271 |
| 2016/0200276 | A1* | 7/2016 | Diewald | G01S 13/04 |
| | | | | 342/28 |
| 2017/0039835 | A1* | 2/2017 | Brankovic | H01Q 9/285 |
| 2018/0170213 | A1* | 6/2018 | Lu-Dac | B60N 2/002 |

FOREIGN PATENT DOCUMENTS

| | | |
|---|---|---|
| WO | 20190026076 A1 | 2/2019 |
| WO | 20190238575 A1 | 12/2019 |

OTHER PUBLICATIONS

International Written Opinion corresponding to International Application PCT/EP2021/051560 dated Apr. 6, 2021; 6 pages.

* cited by examiner

METHOD OF OPERATING A RADAR SENSOR SYSTEM FOR VITAL SIGN DETECTION WITH ELIMINATION OF SIGNALS EXCITED BY INTERFERING MOVEMENTS

TECHNICAL FIELD

The invention relates to a method of operating a radar sensor system for detecting vital signs in an interior of a vehicle, to a radar sensor system configured for automatically executing such method and a software module enabling automatically executing the method.

BACKGROUND

Vehicle interior occupant sensing technologies are nowadays widely used in vehicles, in particular in passenger cars, for instance for vehicle seat occupancy detection for seat belt reminder (SBR) systems, anti-theft alarm and, particularly, for detection of left-behind pets and/or children and/or vital sign monitoring.

It is known in the art to use radar technology for automotive seat occupant detection systems. Occupancy sensors based on radar technology offer advantages in comparison to other occupancy detection methods as their operation is contact-free and unnoticeable for vehicle occupants. Moreover, radar sensors can easily be integrated in the vehicle interior, for example behind plastic, plastic covers and diverse materials such as textiles, wood, glass, and so forth.

From U.S. Pat. No. 6,753,780 B2 a motion sensing system and method is known for detecting an occupant in a vehicle with enhanced sensitivity to detect small movement, such as movement caused by heartbeat and breathing of an occupant. The system includes a radar motion sensor located in a compartment of the vehicle. The radar sensor transmits and receives signals within the compartment and generates sensed signals. The system has a controller for converting the sensed signals to a frequency domain. The controller further processes the frequency domain of sensed signals and determines the presence of movement of an occupant due to one of heartbeat and breathing of the occupant. To this end, the controller compares the frequency domain of sensed signals within the frequency range to a predetermined frequency characteristic, and further identifies a frequency of the sensed signals indicative of movement of an occupant due to one of heartbeat and breathing.

WO 2019/238575 A1 describes a radar sensor system and a method of operating the radar sensor system for detecting an occupancy in an interior of a vehicle with vital sign monitoring. The radar sensor system comprises a radar transmitting unit, a radar receiving unit and a signal processing and control unit.

WO 2015/140333 A1 describes a method for ascertaining whether an unattended child is present within an automotive vehicle. The method uses a radar sensor system comprising a transmitter, and at least one sensor and processing circuitry, and exploits a breathing motion detected by radar signals, for instance by applying autocorrelation and peak finding. The method comprises the steps of: illuminating at least one occupiable position within the vehicle with radiation, the radiation exhibiting multiple frequencies; generating radar sensor signals from radiation reflected as a result of the transmitted radiation, a plurality of the radar sensor signals corresponding to different frequencies; operating the processing circuitry for generating, based on the radar sensor signals, a first indicator value, for instance R-value, the first indicator value indicating a degree of motion associated with the occupiable position; determining whether the first indicator value satisfies a first predetermined criterion; if the first indicator value satisfies the first predetermined criterion, generating, based on radar sensor signals, a second indicator value, the second indicator value indicating a degree of repetitive pattern within the radar sensor signals, for instance breathing pattern; and determining that an unattended child is present within the automotive vehicle if the second indicator value satisfies a second predetermined criterion.

The second indicator value may comprise a breathing signature representing the extent to which the sensor signals indicate that motion indicative of infant breathing child is detected.

Hence, it is known in the art that a presence of a single vehicle passenger can be detected by conducting electromagnetic measurements such as Doppler radar techniques to measure, for instance, the passenger's breathing or heartbeat. Unfortunately, received radar waves are corrupted with noise if, for instance, a vehicle is driving on a road with an uneven road profile, by vibrations from a running car engine or by wind gusts. This noise, which could be of high amplitude compared to the signal of a passenger that is desired to detect will inevitably lead to an increased number of false alarms, i.e. falls positives or false negatives.

It has therefore been proposed in the art to employ additional sensors that are sensitive to vehicle movements for distinguishing between a vital signal portion and a signal portion induced by vehicle movement.

By way of example, WO 2016/038148 A1 describes a method for sensing an occupancy status within an automotive vehicle. The method uses a radar sensor system having an antenna system, at least one sensor and processing circuitry. The method comprises a step of illuminating, using the antenna system, at least one occupiable position within the vehicle with an outgoing radar signal; a step of receiving, using the at least one sensor, at least one sensor signal reflected as a result of the outgoing radar signal; a step of obtaining accelerometer data value from at least one accelerometer, wherein the accelerometer data contain information regarding vibration or motion of the automotive vehicle and a step of supplying the accelerometer data to the processing circuitry; and a step of operating the processing circuitry for generating, based on the at least one sensor signal and on the accelerometer data, one or more occupancy status signals, wherein the occupancy status signal indicates a property related to the at least one occupiable position.

The method includes accelerometer data to a classification software of the radar sensor system and is therefore able to compensate for motion or vibration of the vehicle. The information regarding vibration or motion can be taken into consideration when a classification (interior human detection) algorithm needs to classify. This information can help to filter out exterior influences that might falsify the classification (passing traffic, wind shakes, various vibrations of the engine or any exterior event leading to a vehicle movement).

SUMMARY

It is therefore an object of the invention to provide a method of vital sign monitoring using radar technology, in particular for robust vital sign monitoring in an interior of a vehicle, which is capable of reliably and robustly distinguishing between signals related to an occupant positioned in a specific region of interest in the vehicle interior and disturbing signals caused by vehicle interior events and/or events outside the vehicle, such as vehicle or sensor shaking induced by rough road, strong wind gusts or engine vibrations or deliberate interaction like shaking.

In one aspect of the present invention, the object is achieved by a method of operating a radar sensor system that is configured to determine range and velocity (i.e. Doppler) information from radar waves reflected by a scene in an interior of a vehicle for vital sign detection.

The method comprises at least the following steps, which are to be executed iteratively, while illuminating the interior of the vehicle with radar waves by the radar sensor system:
  receiving radar waves reflected from the scene,
  removing signals that are representative of a static portion of the scene from range signals obtained from the received radar waves for deriving dynamic range signals that are assigned to a plurality of range bins,
  select a plurality of predefined groups of range bins out of the plurality of range bins, wherein the groups are separated by at least one range bin,
  retrieve real values of range signals assigned to each of the range bins of the selected predefined groups of range bins,
  average the retrieved real values over a predefined period of time to form range signal buffers,
  determine a Doppler frequency for each range bin of the plurality of predefined groups of range bins,
  derive a statistic quantity from the determined Doppler frequencies representing a dominant frequency,
  compare the dominant frequency with at least one predetermined condition concerning a predefined characteristic vital sign frequency,
  if the dominant frequency fulfills all predetermined conditions, calculate a plurality of correlation coefficients, one correlation coefficient for each possible pair of range signal buffers,
  group the correlation coefficients into at least two groups depending on the range bins to which the range signals of each possible pair of range signal buffers have been assigned,
  compare each correlation coefficient with a group-specific threshold value and assign predetermined numerical values to each correlation coefficient depending on the outcome of the comparison,
  for each group of correlation coefficients, calculate a numerical indicator value based on the predetermined numerical values that have been assigned to each correlation coefficient of the specific group,
  compare each numerical indicator value to a predetermined group-specific indicator value threshold, and
  generate an output signal based on a result of the comparison for each group.

The phrase "configured to", as used in this application, shall in particular be understood as being specifically programmed, laid out, furnished or arranged.

The proposed method for distinguishing exterior disturbances from vital signs in an interior automotive radar system uses a combination of range and Doppler properties of the received signals. First, the reflected and received signal is decomposed into range and velocity information, to measure the movement over time in specified range gates (bins) and evaluate the similarities between them. Based on the characteristics of similar behaving range bins, it can be decided whether any detected movement is related to an internal or external disturbance or not. By that, a robust vital sign monitoring method using a radar sensor system can be provided.

The output signal can be conveyed to an Automatic Driver Assistance Systems (ADAS) of the vehicle for serving as a support for a decision on further action.

In particular, the invention is applicable with advantage in the automotive sector; i.e. in an interior of a vehicle. The term "automotive", as used in the present application, shall particularly be understood as being suitable for use in vehicles including passenger cars, trucks, semi-trailer trucks and buses. Applications that are considered to especially benefit from the invention is vital sign monitoring in support of an ADAS and unattended child detection.

It is also contemplated to employ the proposed method of vital sign monitoring by operating a radar sensor system for medical usage.

In preferred embodiments of the method, the step of removing signals that are representative of a static portion of the scene comprises
  converting the range signals obtained from the received radar waves from the time domain to the frequency domain, and
  subtracting frequency domain range signals obtained from radar waves received in one of previously executed iterations of the steps, or
  subtracting an average of a plurality of frequency domain range signals obtained from radar waves received in a plurality of previously executed iterations of the steps, or
  applying a high pass filter to the range signals obtained from the received radar waves.

In this way, the static portion of the scene can effectively be removed.

Preferably, the step of determining a Doppler frequency for each range bin of the plurality of predefined groups of range bins comprises converting values from the formed range signal buffers from the time domain to the frequency domain. By that, the Doppler frequency for each range bin can readily and effectively be determined.

In preferred embodiments of the method, the step of deriving a statistic quantity from the determined Doppler frequencies includes calculating a median Doppler frequency value. By calculating a median Doppler frequency, a robust value for a dominant frequency can be derived which is less sensitive to individual fluctuations.

Preferably, the step of calculating a plurality of correlation coefficients comprises to store the calculated correlation coefficients as matrix coefficients in a matrix. This can allow for an especially easy further processing of the calculated correlation coefficients.

Preferably, the step of assigning predetermined numerical values to each correlation coefficient depending on the outcome of the comparison includes assigning predetermined numerical values of either 0 or 1. In this way, similarities of movements over time in the range gates can be worked out in a more pronounced way for improved evaluation. A preferred way of treating the assigned predetermined numerical values of either 0 or 1 is building up a binary matrix.

In preferred embodiments of the method, the step of calculating a numerical indicator value based on the predetermined numerical values that have been assigned to each correlation coefficient of the specific group includes calculating a sum of the numerical values that have been assigned to each correlation coefficient. In this way, a particularly meaningful numerical indicator value can be provided for further evaluation.

In another aspect of the invention, a radar sensor system is provided that comprises a radar transmitter unit that is configured to transmit radar waves towards a scene, a radar receiving unit that is configured for receiving radar waves that have been transmitted by the radar transmitter unit and have been reflected from the scene, an evaluation and control unit that is configured for determining range and velocity information from the radar waves received by the radar receiving unit.

Further, the evaluation and control unit is configured for carrying out steps of any embodiment of the method as disclosed herein.

The benefits described in context with the disclosed method of operating a radar sensor system for vital sign detection applied to the proposed radar sensor system to the full extent.

In preferred embodiments of the radar sensor system, the radar transmitter unit is configured for transmitting frequency-modulated continuous radar waves (FMCW) or for transmitting radar waves that are modulated according to a frequency-shift keying scheme. In this way, range and velocity information can readily be obtained from the radar waves received by the radar receiving unit. Further, a lot of experience with such radar sensor system hardware can be relied on.

In yet another aspect of the invention, a software module for controlling an automatic execution of steps of any embodiment of the method disclosed herein is provided.

The method steps to be conducted are converted into a program code of the software module, wherein the program code is implementable in a non-transitory computer-readable medium, such as a digital memory unit of the radar sensor system or a separate control unit and is executable by a processor unit of the radar sensor system or a separate control unit. Preferably, the digital memory unit and/or processor unit may be a digital memory unit and/or a processing unit of the evaluation and control unit of the radar sensor system. The processor unit may, alternatively or supplementary, be another processor unit that is especially assigned to execute at least some of the method steps.

The software module can enable a robust and reliable automatic execution of the method and can allow for a fast modification of method steps.

These and other aspects of the invention will be apparent from and elucidated with reference to the embodiments described hereinafter.

It shall be pointed out that the features and measures detailed individually in the preceding description can be combined with one another in any technically meaningful manner and show further embodiments of the invention. The description characterizes and specifies at least one embodiment of the invention in particular in connection with the figures.

BRIEF DESCRIPTION OF THE DRAWINGS

Further details and advantages of the present invention will be apparent from the following detailed description of not limiting embodiments with reference to the attached drawings, wherein.

DETAILED DESCRIPTION

Figure 1:
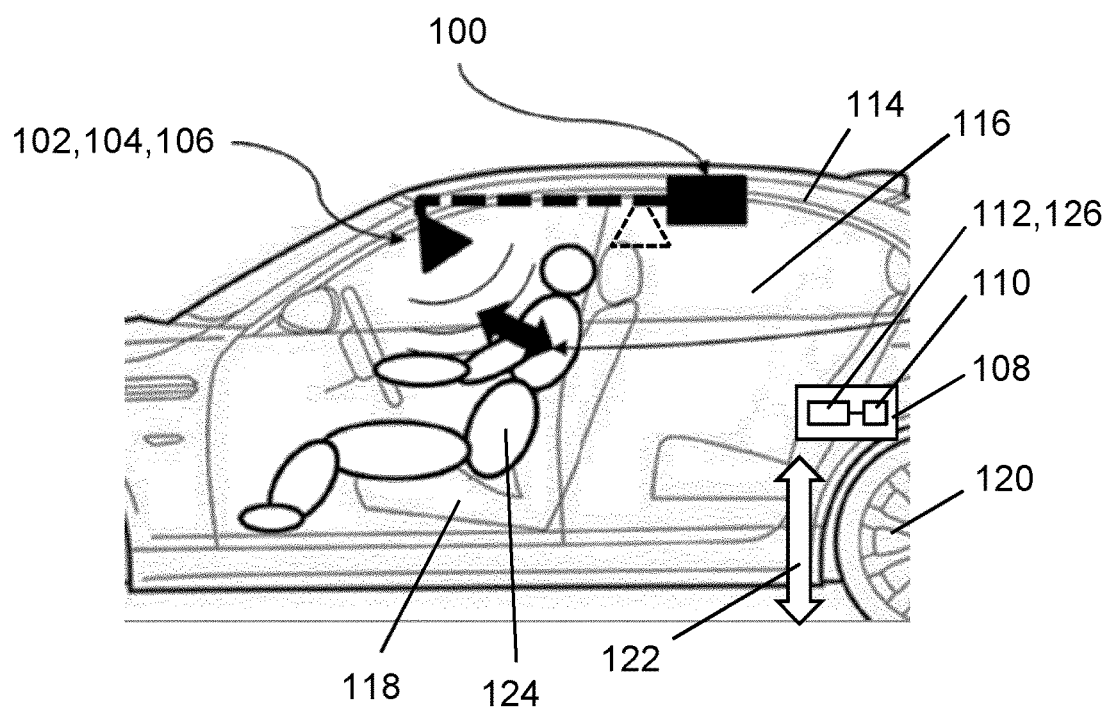
FIG. 1 schematically illustrates a radar sensor system in accordance with the invention for detecting passenger vital signs in an interior of a vehicle in a side view, installed in the vehicle.

FIG. 1 schematically illustrates, in a side view, a possible embodiment of a radar sensor system 100 in accordance with an embodiment of the invention. The radar sensor system 100 is installed in an interior 116 of a vehicle 114, which is designed as a passenger car. The radar sensor system 100 is configured for operation in the interior 116 of the vehicle 114, and particularly for determining range and velocity information from radar waves reflected by a scene given by an interior 116 of the vehicle 114, for vital sign detection by an automotive vehicle interior sensing system.

A person 124 located in the interior 116 of the vehicle 114 is the driver, who is occupying the driver's seat 118 of the vehicle 114. The vehicle 114 is driving on a roadway, whose roughness causes vertical motion 122 of vehicle wheels 120. The vertical motion 122 of the wheels 120 is transferred to a body of the vehicle 114 via a vehicle suspension system (not shown), generating forced vibrations of the driver's seat 118 (and other seats as well) and the person 124 occupying the driver's seat 118. Additional forced vibrations are induced by mechanical vibrations of a running engine of the vehicle 114.

The radar sensor system 100 comprises a radar transmitter unit 102, a radar receiving unit 104 and an evaluation and control unit 108 that is connected by data links and signal lines to both the radar transmitter unit 102 and the radar receiving unit 104 and which may be positioned in the vehicle 114 remote from the radar transmitter unit 102 and the radar receiving unit 104. The radar transmitter unit 102 of the radar sensor system 100 includes a radar transmit antenna (not shown) that is directed towards a scene given by the interior 116 of the vehicle 114 and is configured for transmitting frequency-modulated continuous radar waves towards the scene. In other embodiments, the radar transmitter unit may be configured for transmitting radar waves that are modulated according to a frequency-shift keying scheme. In the embodiment shown in FIG. 1, the radar transmitter unit 102 and the radar receiving unit 104 are shown to be arranged in the front part of the vehicle in front of the driver/passenger (e.g. in the vicinity of the windshield). The skilled person will however understand that other mounting positions for the transmitter and receiver units are possible. The radar transmitter unit 102 and the radar receiving unit 104 may e.g. be positioned more centrally in the vehicle compartment, e.g. above the driver and/or passenger. This position is schematically represented in FIG. 1 in dashed line.

The radar receiving unit 104 includes a radar receiving antenna (not shown) that is also directed towards the scene. The radar receiving unit 104 is configured for receiving radar waves, which have been transmitted by the radar transmitter unit 102 and have been reflected from the scene, in particular by the driver's chest.

The radar transmit antenna and the radar receiving antenna are co-located in a monostatic, bistatic of multistatic arrangement. In this specific embodiment, the radar transmitter unit 102 and the radar receiving unit 104 form an integral part of a transceiver unit 106. In other embodiments, the radar transmitter unit 102 and the radar receiving unit 104 may be designed as separate units.

The evaluation and control unit 108 is configured for determining range and velocity information from the radar waves received by the radar receiving unit 104. The evaluation and control unit 108 comprises a processor unit 110 and a digital data memory unit 116 to which the processor unit 110 has data access.

The radar sensor system 100 is configured for vital sign detection that are given by a breathing motion of the driver or passenger, characterized by an amplitude and a breathing frequency. The radar sensor system 100 is sensitive to a relative motion between the radar transceiver unit 106 and the driver's chest. The radar sensor system 100 is also sensitive to a relative motion of the radar transceiver unit 106 to parts within the interior 116 of the vehicle 114.

As a relative movement of the driver's chest with regard to the radar transceiver unit 106 is superimposed by the forced vibrations, so are the range and velocity information determined from radar waves reflected by the driver's chest and received by the radar receiving unit 104.

In order to reliably and robustly distinguishing between radar signals related to an occupant positioned in a specific region of interest in the vehicle interior 116 and disturbing signals caused by vehicle interior events and/or events outside the vehicle 114, such as vehicle or sensor shaking induced by rough road, strong wind gusts or engine vibrations or intentional shaking, the evaluation and control unit 108 is configured for automatic execution of steps of an inventive method of operating the radar sensor system 100 in a controlled way.

To this end, the evaluation and control unit 108 is equipped with a software module 126. The method steps to be conducted are converted into a program code of the software module 126. The program code is implemented in the digital data memory unit 112 of the evaluation and control unit 108 and is executable by the processor unit 110 of the evaluation and control unit 108.

In the following, an embodiment of the method of operation the radar sensor system 100 in the interior 116 of the vehicle 114 will be described with reference to FIG. 1. In preparation of operating the radar sensor system 100, it shall be understood that all involved units and devices are in an operational state and configured as illustrated in FIG. 1.

The steps of the method are to be executed iteratively, while illuminating the interior 116 of the vehicle 114 with radar waves by the radar sensor system 100 as a step 10 of the method.

In a first block 20 of steps (FIG. 2), dynamic range signals assigned to a plurality of range bins are derived.

Figure 3:
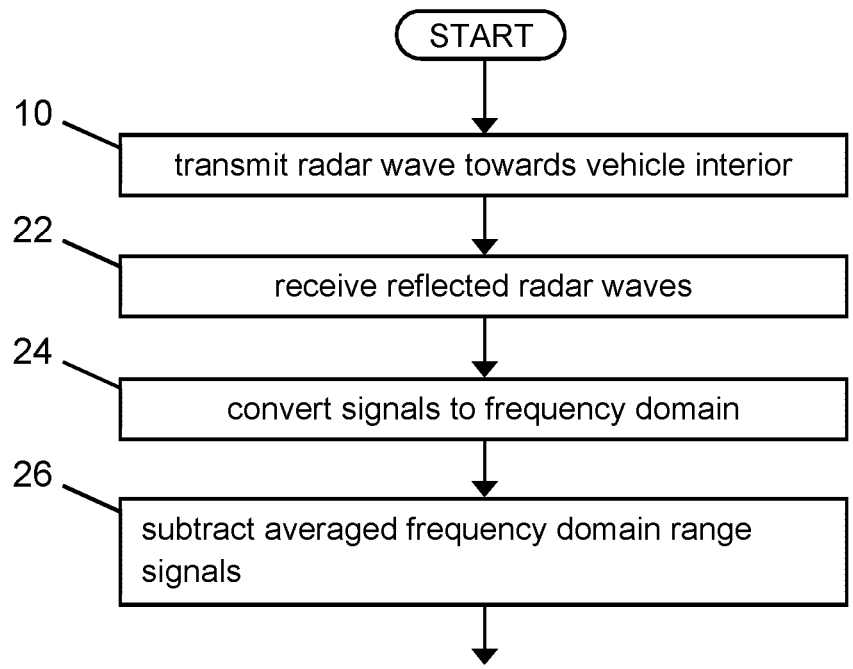
FIG. 3 is a flowchart of a part of the embodiment of the method pursuant to FIG. 2, FIG. 4 schematically shows an intermediate result after executing the part of the method pursuant to FIG. 3.

In a first step 22 of the block 20, radar waves reflected from the scene are received (FIG. 3). In a next step, signals that are representative of a static portion of the scene are removed from range signals obtained from the received radar waves for deriving the dynamic range signals assigned to the plurality of range bins. To this end, the range signals obtained from the received radar waves are converted from the time domain to the frequency domain in a step 24, for instance by applying a Fast Fourier Transform (FFT), followed by a step 26 of subtracting an average of a plurality of frequency domain range signals obtained from radar waves received in a plurality of previously executed iterations of the steps. A result for the (dynamic) range FFT is exemplarily shown in FIG. 4.

In a next block 30 of steps (FIG. 2), preprocessing of the range FFT signals is carried out.

Figure 4:
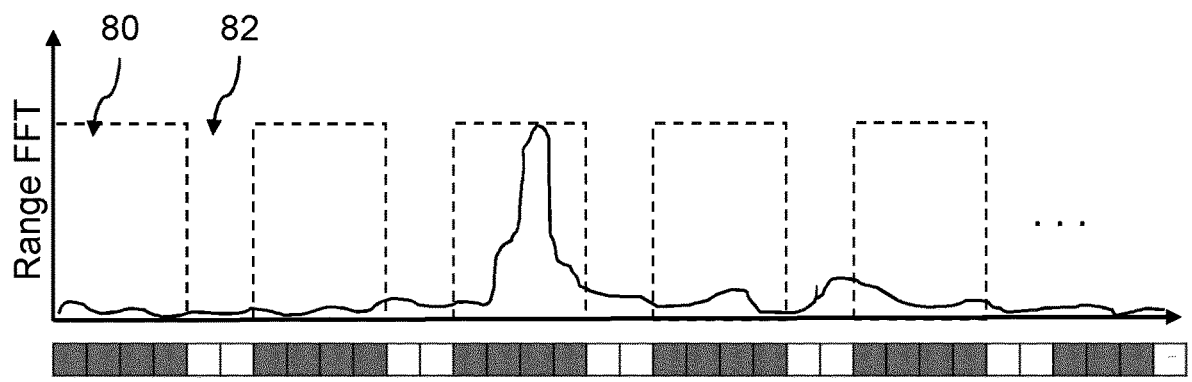
Figure 5:
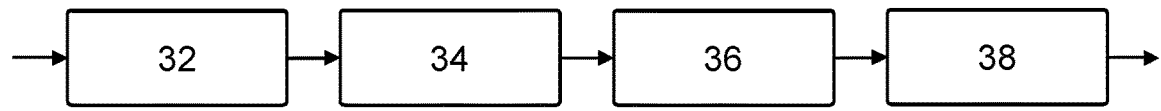
FIG. 5 is a flowchart of another part of the embodiment of the method pursuant to FIG. 2.

As a next step 32 of this block 30 of steps, a plurality of predefined groups of range bins 80 out of the plurality of range bins is selected (FIG. 5), wherein the groups are separated by two guard range bins 82, as is shown in FIG. 4. In another step 34, real values of range signals assigned to each of the range bins 80 of the selected predefined groups of range bins are retrieved, for instance from the digital data memory unit 112. Then, the retrieved real values are averaged over a predefined period of time in one step 36 and range signal buffers are formed in another step 38.

In a further block 40 of steps (FIG. 2) a dominant frequency of the real values of the range signals is derived.

In this block 40 of steps, a Doppler frequency for each range bin 80 of the plurality of predefined groups of range bins is determined. This is carried out by converting values from the formed range signal buffers from the time domain to the frequency domain, for instance by applying an FFT. From the determined Doppler frequencies, a statistic quantity is then derived by determining a median Doppler frequency value, which is taken as the dominant frequency.

Figure 8:
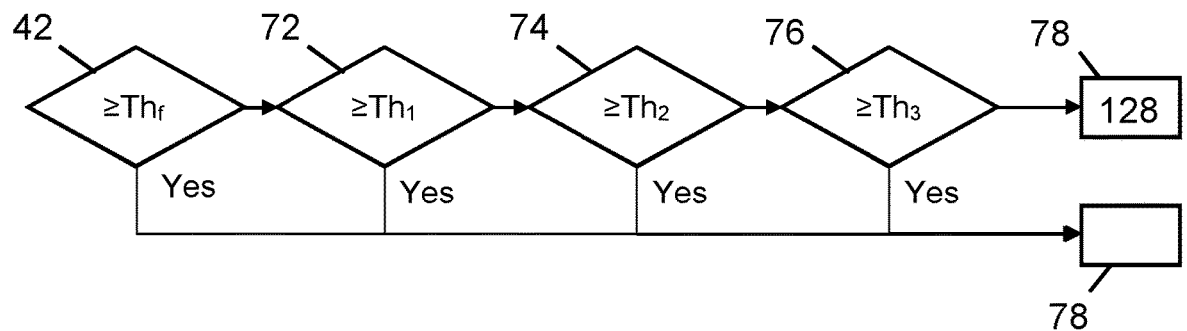
FIG. 8 is a flow chart of another part of the embodiment of the method pursuant to FIG. 2.

The determined dominant frequency is checked against a predetermined condition concerning a predefined characteristic vital sign frequency, which is given by the determined dominant frequency falling below an upper limit $Th_f$ for the breathing frequency, in a step 42 of comparison (FIG. 8). If the determined dominant frequency fails to fulfill this predetermined condition, the received radar waves are considered to originate from sources other than vital signs.

Figure 2:
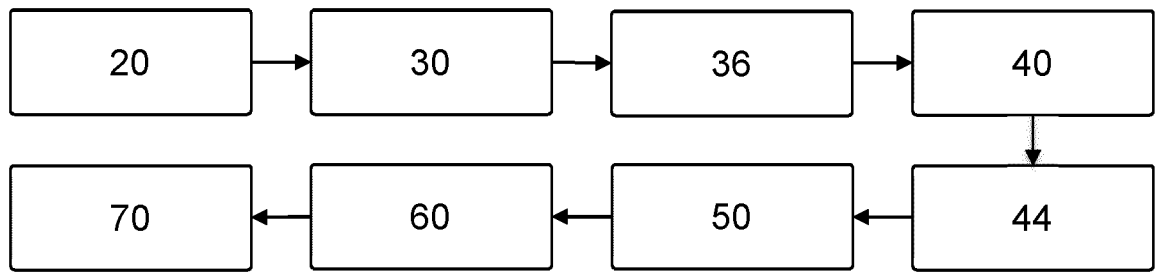
FIG. 2 is an overview block picture of an embodiment of the method in accordance with the invention of operating the radar sensor system pursuant to FIG. 1.
Figure 7:
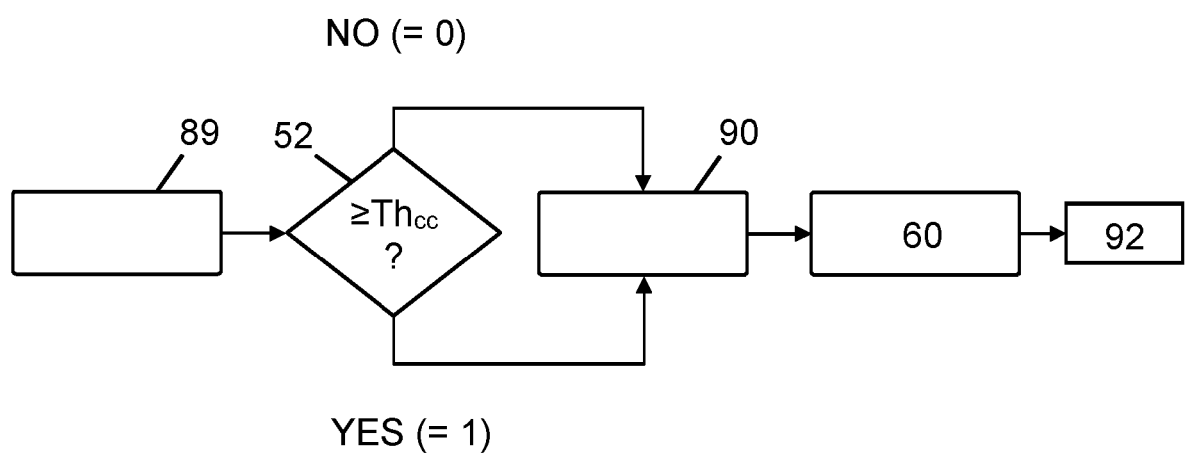
FIG. 7 is a flowchart of another part of the embodiment of the method pursuant to FIG. 2.

If the determined dominant frequency fulfills these predetermined conditions, a plurality of correlation coefficients is calculated in another step 44, one correlation coefficient for each possible pair of range signal buffers (FIG. 2). Further, the calculated correlation coefficients are stored as matrix elements in a matrix 89 (FIG. 7). The matrix may reside in the digital data memory unit 112 of the evaluation and control unit 108.

Figure 6:
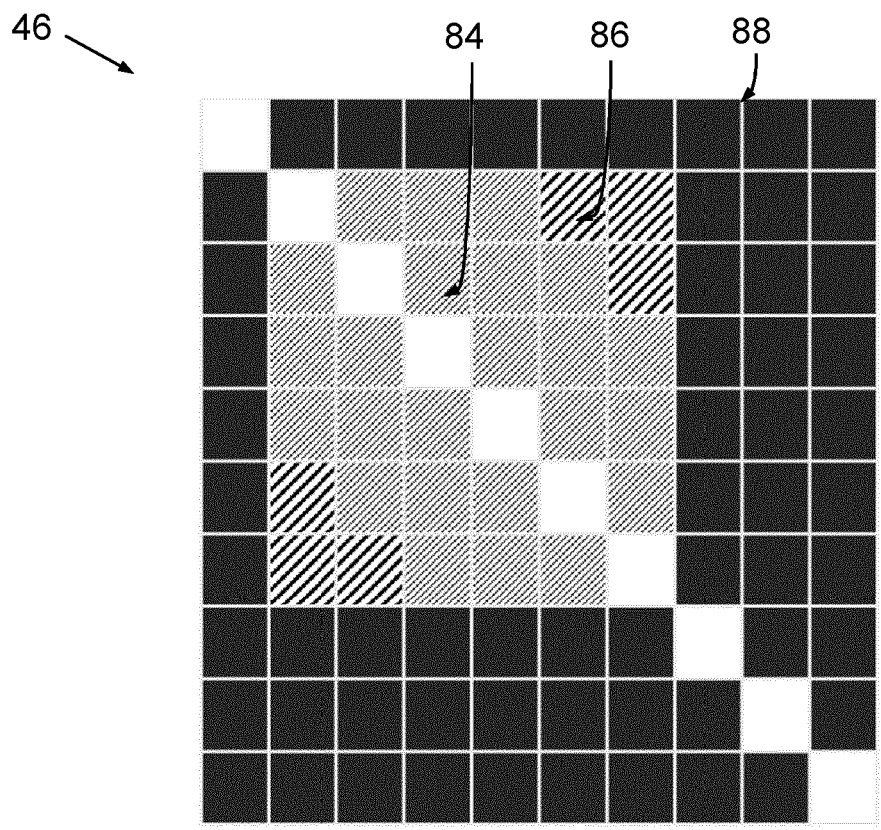
FIG. 6 shows an exemplary region mask.

In a next step 46, the correlation coefficients are grouped, depending on the range bins to which the range signals of each possible pair of range signal buffers have been assigned. In this specific embodiment, the correlation coefficients are grouped into three groups, which may represent a range region 84 covering the vehicle interior 116, a region 86 of interior ranges whose distance is large, and an exterior region 88. In FIG. 6, the grouping of the correlation coefficients is illustrated in a two-dimensional array forming a region mask. In other embodiments, the correlation coefficients may be grouped into a different number of groups.

In a further block 50 of steps (FIG. 2) predetermined numerical values are assigned to the grouped correlation coefficients.

In a step 52 of this block 50 of steps (FIG. 7), each correlation coefficient is compared with a group-specific threshold value, and a predetermined numerical value is assigned to each correlation coefficient depending on the outcome of the comparison. In this specific embodiment, a predetermined numerical value of 0 is assigned if the correlation coefficient is smaller than the group-specific threshold value $Th_{cc}$, and the predetermined numerical value of 1 is assigned if the correlation coefficient is equal to or larger than the group-specific threshold value. The result of the step 52 of assigning the predetermined numerical values to the correlation coefficients of the matrix 89 is a binary matrix 90 of same size.

All predetermined/predefined values, threshold values and conditions mentioned herein may reside in the digital data memory unit 112 of the electronic control unit 108 and can readily be retrieved by the processor unit 110 of the electronic control unit 108.

In a next step 60, for each group of correlation coefficients, a numerical indicator value 92 is calculated based on the predetermined numerical values that have been assigned to each correlation coefficient of the specific group. In this specific embodiment, this is carried out by calculating a sum of the numerical values that have been assigned to each correlation coefficient of a specific group; i.e. by summing up the "1"s for each group in the region mask.

Then, a further block 70 of steps is executed for decision-making (FIG. 2).

In steps 72, 74, 76 of this block 70 of steps (FIG. 8), each numerical indicator value 92 is compared to a predetermined group-specific indicator value threshold $Th_1$, $Th_2$, $Th_3$. The indicator value thresholds $Th_1$, $Th_2$, $Th_3$ are suitably defined in such a way that the method is sensitive to correlation in the interior 116 of the vehicle 114 as well as to distinguishing between movement of a person within the vehicle 114 and an interior or exterior interfering movement.

In a final step 78, an output signal 128 is generated based on a result of the comparison for each group of correlation coefficients. Only if each numerical indicator value 92 falls below the predetermined group-specific indicator value threshold $Th_1$, $Th_2$, $Th_3$ of its group of correlation coefficients, vital sign detection is confirmed and a corresponding output signal 128 is generated. If at least one of the numerical indicator values 92 is equal to or larger than the predetermined group-specific indicator value threshold $Th_1$, $Th_2$, $Th_3$ of its group, vital sign detection is highly improbable, and a different corresponding output signal is generated.

While the invention has been illustrated and described in detail in the drawings and foregoing description, such illustration and description are to be considered illustrative or exemplary and not restrictive; the invention is not limited to the disclosed embodiments.

Other variations to be disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality, which is meant to express a quantity of at least two. The mere fact that certain measures are recited in mutually different dependent claims does not indicate that a combination of these measures cannot be used to advantage. Any reference signs in the claims should not be construed as limiting scope.

The invention claimed is:

1. Method of operating a radar sensor system that is configured to determine range and velocity information from radar waves reflected by a scene in an interior of a vehicle for vital sign detection, the method comprising at least the following steps, which are to be executed iteratively, while illuminating the interior of the vehicle with radar waves by the radar sensor system,
receiving radar waves reflected from the scene,
removing signals that are representative of a static portion of the scene from range signals obtained from the received radar waves for deriving dynamic range signals assigned to a plurality of range bins,
selecting a plurality of predefined groups of range bins out of the plurality of range bins, wherein the groups are separated by at least one range bin,
retrieving real values of range signals assigned to each of the range bins of the selected predefined groups of range bins,
averaging the retrieved real values over a predefined period of time to form range signal buffers,
determining a Doppler frequency for each range bin of the plurality of predefined groups of range bins,
deriving a statistic quantity from the determined Doppler frequencies representing a dominant frequency,
comparing the dominant frequency with at least one predetermined condition concerning a predefined characteristic vital sign frequency,
if the dominant frequency fulfills all predetermined conditions, calculating a plurality of correlation coefficients, one correlation coefficient for each possible pair of range signal buffers,
grouping the correlation coefficients into at least two groups depending on the range bins to which the range signals of each possible pair of range signal buffers have been assigned,
comparing each correlation coefficient with a group-specific threshold value and assign predetermined numerical values to each correlation coefficient depending on the outcome of the comparison,
for each group of correlation coefficients, calculating a numerical indicator value based on the predetermined numerical values that have been assigned to each correlation coefficient of the specific group,
comparing each numerical indicator value to a predetermined group-specific indicator value threshold, and
generating an output signal based on a result of the comparison for each group.

2. The method as claimed in claim 1, wherein the step of removing signals that are representative of a static portion of the scene comprises:
converting the range signals obtained from the received radar waves from the time domain to the frequency domain, and
subtracting frequency domain range signals obtained from radar waves received in one of previously executed iterations of the steps, or
subtracting an average of a plurality of frequency domain range signals obtained from radar waves received in a plurality of previously executed iterations of the steps, or
applying a high pass filter to the range signals obtained from the received radar waves.

3. The method as claimed in claim 1, wherein the step of determining a Doppler frequency for each range bin of the plurality of predefined groups of range bins comprises converting values from the formed range signal buffers from the time domain to the frequency domain.

4. The method as claimed in claim 1, wherein the step of deriving a statistic quantity from the determined Doppler frequencies includes determining a median Doppler frequency value.

5. The method as claimed in claim 1, wherein the step of calculating a plurality of correlation coefficients comprises to store the calculated correlation coefficients as matrix coefficients in a matrix.

6. The method as claimed in claim 1, wherein the step of assigning predetermined numerical values to each correlation coefficient depending on the outcome of the comparison includes assigning predetermined numerical values of either 0 or 1.

7. The method as claimed in claim 1, wherein the step of calculating a numerical indicator value based on the predetermined numerical values that have been assigned to each correlation coefficient of the specific group includes calculating a sum of the numerical values that have been assigned to each correlation coefficient.

8. A radar sensor system, comprising:
- a radar transmitter unit that is configured to transmit radar waves towards a scene,
- a radar receiving unit that is configured for receiving radar waves that have been transmitted by the radar transmitter unit and have been reflected from the scene,
- an evaluation and control unit that is configured for determining range and velocity information from the radar waves received by the radar receiving unit,
- wherein the evaluation and control unit is further configured for carrying out the method as claimed in in claim 1.

9. The radar sensor system as claimed in claim 8, wherein the radar transmitter unit is configured for transmitting frequency-modulated continuous radar waves or for transmitting radar waves that are modulated according to a frequency-shift keying scheme.

10. A non-transitory, computer-readable medium having stored thereon a software module for controlling automatic execution of the method as claimed in claim 1, wherein the software module comprises program code that is executable by a processor unit of a radar sensor system or by a separate control unit for the radar system to carry out the method, wherein the radar sensor system comprises:
- a radar transmitter unit that is configured to transmit radar waves towards a scene,
- a radar receiving unit that is configured for receiving radar waves that have been transmitted by the radar transmitter unit and have been reflected from the scene, and
- an evaluation and control unit that is configured for carrying out the method to determine range and velocity information from the radar waves received by the radar receiving unit.

* * * * *